(12) United States Patent
Nishimoto et al.

(10) Patent No.: US 7,959,936 B2
(45) Date of Patent: Jun. 14, 2011

(54) EMULSIFICATIONS-STABLE PESTICIDAL COMPOSITION

(75) Inventors: Koichi Nishimoto, Kyoto (JP); Kunitoshi Watanabe, Tokyo (JP); Toshiyasu Shizawa, Tokyo (JP)

(73) Assignee: Syngenta Crop Protection, Inc., Greensboro, NC (US)

( * ) Notice: Subject to any disclaimer, the term of this patent is extended or adjusted under 35 U.S.C. 154(b) by 1158 days.

(21) Appl. No.: 10/570,100

(22) PCT Filed: Sep. 24, 2004

(86) PCT No.: PCT/EP2004/010744
§ 371 (c)(1),
(2), (4) Date: Oct. 10, 2006

(87) PCT Pub. No.: WO2005/029960
PCT Pub. Date: Apr. 7, 2005

(65) Prior Publication Data
US 2007/0078110 A1 Apr. 5, 2007

(30) Foreign Application Priority Data
Sep. 25, 2003 (JP) ................. 2003-334013

(51) Int. Cl.
*A01N 25/00* (2006.01)
*A01N 25/22* (2006.01)
*A01N 25/06* (2006.01)
*A01N 25/08* (2006.01)

(52) U.S. Cl. ...................................... 424/405

(58) Field of Classification Search .................. 424/405
See application file for complete search history.

(56) References Cited

U.S. PATENT DOCUMENTS

| 4,160,029 A | 7/1979 | Duyfjes |
| 5,013,748 A | 5/1991 | Radtke et al. |
| 5,139,773 A * | 8/1992 | Tadros .................. 514/315 |
| 5,698,191 A * | 12/1997 | Wiersma et al. .......... 424/78.09 |

FOREIGN PATENT DOCUMENTS

| EP | 0095242 | 11/1983 |
| WO | WO 0245507 A2 * | 6/2002 |

* cited by examiner

*Primary Examiner* — Fereydoun G Sajjadi
*Assistant Examiner* — Courtney Brown
(74) *Attorney, Agent, or Firm* — William A. Teoli, Jr.

(57) ABSTRACT

An object of the present invention is to provide an emulsification-stable pesticidal composition having ant-control, rot-control and mildew-control effects. Another object of the present invention is to provide a composition having pesticidal effects, and particularly antimicrobial effects, for protecting industrial materials such as wood, pulp, paper, fibers, adhesives, films subject to deterioration (rotting) and contamination by insects and particularly by microorganisms. A pesticidal composition is used that comprises an emulsification stabilizer selected from the group consisting of lactic acid, glycolic acid, citric acid, succinic acid, benzoic acid and a mixture thereof, a fungicide like 2-(thiazol-4ine)benzimidazole; a further triazole-based fungicide component, a pyrethroid insecticide component or a (thia) nicotinyl insecticide or another insecticide component, a mixed solvent comprising a glycol-based solvent and methyl pyrrolidone, and a surfactant.

14 Claims, No Drawings

EMULSIFICATIONS-STABLE PESTICIDAL COMPOSITION

This application is a 371 of International Application No. PCT/EP2004/010744 filed Sep. 24, 2004, which claims priority to JP 2003-334013, filed Sep. 25, 2003, the contents of which are incorporated herein by reference.

The present invention relates to an emulsification-stable pesticidal composition mainly having ant-control, termit-control, rot-control and mildew-control effects, and more particularly, to a composition capable of maintaining a uniform dispersion of active ingredients in a diluted aqueous solution over a long period of time when using the pesticidal composition of the present invention as an emulsion. In addition, the present invention relates to a composition having pesticidal effects, and particularly antimicrobial effects, for protecting industrial materials such as wood, pulp, paper, fibers, adhesives and films subject to deterioration (rotting) and contamination by insects and particularly by microorganisms. Moreover, the present invention relates to a composition that prevents insect damage caused for example by wood-eating pests, including termite damage and particularly ant damage.

The present invention relates also to a method for protecting industrial materials by controlling pests responsible for industrial materials damages, which comprises applying a pesticidal composition according to the instant invention to said industrial materials.

The present invention relates also to the use of a pesticidal composition according to the instant invention as ant-control agent, termit-control agent, rot-control agent or mildew-control agent.

There has recently been a growing trend towards increased emphasis on the resolution and accommodation of common global problems represented by such problems as deforestation, the greenhouse effect, destruction of the ozone layer and environmental pollution. On the other hand, in advanced countries including Japan, there is growing concern over the effects on the health of people and their pets of interior air contamination by chemical substances in newly constructed or reformed residences and building. This is mainly the result of chemical substances dispersed (or volatilized) from building materials, furniture and contained articles such as household items, and cause conditions such as dizziness, headache and painful irritation of the eyes, nose and throat. There were 13 types of volatile substances initially defined as causative substances of these conditions. However, it was later determined from the results of subsequent investigations that the majority of these conditions are caused by solvents (organic chemical substances).

On the other hand, numerous compounds have been invented and marketed thus far for use as insecticides, and as antimicrobials in particular. However, there are very few universally effective compounds that can be provided for practical use against any type of microorganism in consideration of such factors as economy, safety during and after use and contamination. Naturally, if only considering antimicrobial properties, antimicrobials are effective against numerous microorganisms classified as bacteria, yeasts, molds and so forth by increasing their concentration. However, highly concentrated antimicrobials are disadvantageous in terms of such factors as economy and environmental contamination.

For example, although benzethonium chloride which is typified by quaternary ammonium salt, is adequately effective against pathogens (bacteria) such as *Escherichia coli* and *Salmonella typhi* even when used practically as an aqueous solution having a concentration of 0.01% by mass, it is not effective against molds such as *Aspergillus* spp. and *Penicillium* spp. unless it is used practically at a concentration of 3 to 5% by mass.

Thus, in order to obtain broad-spectrum pesticidal efficacy against a diverse range of pests and microorganisms, it is necessary to use a mixture of a plurality of compounds having different effects.

Accordingly, chemical compounds used as both insecticides and antimicrobials are preferably compounds that do not cause environmental destruction or environmental contamination and do not have a detrimental effect on people, livestock, fish, beneficial insects, plants and so forth. In addition, they preferably are capable of demonstrating a potent effect even when used in small amounts.

One example of a chemical substance that satisfies these requirements is 2-(thiazol-4-ine)benzimidazole (or 2-(4-thiazolyl)-1H-benzimidazole; generic name: thiabendazole). This thiabendazole is used, for example, by adding to or mixing with paints, resins, adhesives, paper products and so forth as a mildew-control agent. In addition, it is also used as an agricultural chemical, food additive (in citrus fruit, bananas and so forth) and animal insect repellent due to its high level of safety.

Moreover, since it also has adequate and stable heat resistance, it is also used as a mildew-control agent that can be blended into resins.

However, thiabendazole has poor solubility and is difficult to formulate into a preparation. Namely, thiabendazole is practically insoluble in water and only slightly soluble in typical industrial solvents such as xylene and petroleum-based solvents. Although it demonstrates comparatively satisfactory solubility in short-chain alcohols having a small number of carbon atoms such as methyl alcohol, such solvents are not practical since they have a strong solvent odor (alcohol odor), are flammable, have restrictions on handling volume and require considerable precautions during handling.

Therefore, there were many cases in the past in which thiabendazole was used in the form of a wettable powder by suspending in water. However, due to the considerably large particle size when suspended in water, it was difficult to maintain it in a uniformly dispersed state. Moreover, thiabendazole has also been formulated by dispersing in water with a surfactant. However, the dispersion breaks down when allowed to stand undisturbed for a long period of time, thereby resulting in the risk of causing liquid phase separation over time.

On the other hand, an emulsion having a small particle size during suspension can be obtained by mixing and suspending thiabendazole, a solvent compatible with thiabendazole and a surfactant. For example, a single liquid phase emulsion can be obtained by mixing an alcohol solvent such as a glycol-based solvent comparatively compatible with thiabendazole, or a solvent such as methyl pyrrolidone that is highly soluble in water and an organic solvent, with thiabendazole, followed by blending in a suitable surfactant. However, although these emulsions are typically used by diluting with water, when diluted with water, the uniformity of the emulsion is lost, resulting in settling, precipitation and liquid phase separation either immediately or in a short period of time.

Although solid antimicrobial binders containing thiabendazole have been known so far, a pesticidal emulsion containing thiabendazole, capable of maintaining a uniform emulsion property without the occurrence of settling, precipitation or liquid phase separation is not yet known.

Therefore, an object of the present invention is to develop an emulsification stabilizer used in an emulsion containing the aforementioned thiabendazole. This emulsification stabilizer has the effects of maintaining a uniform emulsion and inhibiting settling, precipitation and liquid phase separation even if the emulsion is diluted with water. The resulting emulsion demonstrates superior permeability into the material to which the emulsion is added while also exhibiting superior adhesive effects and effects that prevent treatment unevenness as compared with wettable powders and aqueous suspensions.

In addition, an object of the present invention is to provide a stabilized emulsion composition that is added to industrial materials such as wood, pulp, paper, fibers, adhesives and film, their intermediate materials and their finished products, is capable of preventing deterioration and contamination by microorganisms, exhibits superior workability and can be expected to yield a uniformly treated finish and reliable rot-control and mildew-control effects.

Moreover, an object of the present invention is to provide a satisfactory combination of emulsification stabilizer, solvent and surfactant, etc. that realizes emulsification stability of thiabendazole despite its poor solubility and difficulty in formulating into a preparation.

In addition, an object of the present invention is to provide a pesticidal composition which is able to realize satisfactory emulsification stability in the cases where it is even more difficult to prepare a solution by containing a plurality of active ingredients including thiabendazole, triazole-based fungicides and other insecticide components having different solubilities.

As a result of conducting extensive research to achieve the aforementioned objects, the inventors of the present invention found that, by mixing a specific emulsification stabilizer like lactic acid into a composition containing an active ingredient like thiabendazole, solvents like a glycol-based solvent and methyl pyrrolidone, and a surfactant, emulsification stability of the aforementioned composition can be obtained, thereby leading to completion of the present invention.

Namely, the present invention relates to a pesticidal composition comprising:
an emulsification stabilizer selected from the group consisting of lactic acid, glycolic acid, citric acid, succinic acid, benzoic acid or a mixture thereof,
2-(thiazol-4-ine)benzimidazole,
a mixed solvent of glycol-based solvent and methyl pyrrolidone, and
a surfactant.

In addition, the present invention also relates to the aforementioned pesticidal composition further containing a triazole fungicide component at a mass ratio of 1:1 to 4:1 between the 2-(thiazol-4-ine)benzimidazole and the triazole fungicide component. Most preferred mass ratio between 2-(thiazol-4-ine)benzimidazole and the triazole component is 2:1 to 3:1.

Moreover, the present invention relates to the aforementioned pesticidal composition further containing a pyrethroid insecticide component selected from cyphenothrin, cypermethrin, permethrin, bifenthrin or mixtures thereof; a (thia)nicotinyl insecticide component selected from imidacloprid, acetamiprid, thiamethoxam, clothianidin or mixtures thereof; another insecticide components selected from etofenprox, silafluofen, fipronil, chlorfenapyr or mixtures thereof.

Furthermore, the present invention also relates to the aforementioned pesticidal composition further containing a pyrethroid insecticide component selected from cyphenothrin, cypermethrin, permethrin, bifenthrin, a (thia)nicotinyl insecticide component selected from imidacloprid, acetamiprid, thiamethoxam, clothianidin, an insecticide component selected from etofenprox, silafluofen, fipronil, chlorfenapyr or mixtures thereof.

The composition of the present invention has hardly any solvent odor and has superior workability.

The composition of the present invention enables uniform treatment without the occurrence of treatment unevenness since it has superior formulation stability without causing separation.

The present invention provides a composition having improved emulsification stability and permeability.

In the case of using the composition of the present invention be diluting in water, work can be carried out efficiently and economically since separation, settling and crystal precipitation hardly occur.

The present invention is able to provide an environmentally-friendly treatment method, treatment agent or treated products.

The composition of the present invention can be expected to demonstrate a high level of ant-control, termit-control, rot-control and mildew-control effects depending on the type of active ingredients contained therein.

Moreover, the composition of the present invention is able to contain a plurality of poorly soluble active ingredients due to its high level of emulsification stability. Thus, numerous and various insecticide effects and antimicrobial effects can be demonstrated with a single composition. Thus, the composition of the present invention is useful as ant-control agent, termit-control agent, rot-control agent or mildew-control agent depending on the type of active ingredients contained therein. In addition, these pesticidal effects can be sustained for a long period of time.

The composition of the present invention contains an emulsification stabilizer, an active ingredient, a solvent and a surfactant. The following provides an explanation of each component. It should be noted that the term "pesticidal composition" used in the present invention includes the meaning of a composition having insecticide, ant poison, antimicrobial, ant-control, rot-control and mildew-control activity capable of eliminating not only insects like ants and termites, but also microorganisms such as bacteria and molds (antimicrobial).

The emulsification stabilizer used in the present invention is used to stabilize emulsification over a long period of time by adjusting the pH of the pesticidal composition of the present invention. The emulsification stabilizer used in the present invention should preferably be, for example, weakly acidic organic carboxylic acid-based emulsification stabilizer having a pKa value (20° C.) of about 2.2 to 4.2, and preferably about 2.5 to 4.0. Examples of this emulsification stabilizer include carboxylic acid-based emulsification stabilizers selected from the group consisting of lactic acid, glycolic acid, citric acid, succinic acid, benzoic acid and mixtures thereof, with lactic acid being particularly preferable. The emulsification stabilizer of the present invention is suitably contained at, for example, 1 to 10% by mass, and preferably 2 to 8% by mass, with respect to the total mass of the pesticidal composition of the present invention. If the contained amount is 1% by mass or more, the pH value of the composition of the present invention can be varied easily, and if the contained amount is 10% by mass or less, the pH value can be varied easily and stability over time can be adequately ensured for the composition of the present invention, thus such mass values being preferably employed.

The active ingredient used in the present invention broadly refers to an ingredient having insecticide effects, antimicrobial effects, insect preventive effects, ant-control effects, rot-control effects, mildew-control effects and microbial preventive effects. Here, insect preventive effects have a broader meaning than insecticide effects, and includes not only insecticide effects, but also repellent effects that prevent insects from approaching. This applies similarly to ant-control, rot-control, mildew-control and microbial preventive effects. The preferred active ingredient used in the present invention is 2-(thiazol-4-ine)benzimidazole (or 2-(4-thiazolyl)-1H-benzimidazole; generic name: thiabendazole). This thiabendazole has superior efficacy against microorganisms such as bacteria, mold and yeasts, and particularly against mold and bacteria. The following provides a summary of the properties of thiabendazole.

TABLE 1

Summary of the properties of thiabendazole

| | | |
|---|---|---|
| Generic name (abbreviation) | Thiabendazole (TBZ) | |
| Chemical structure | 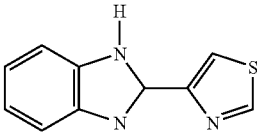 | |
| Physico-chemical properties | Molecular weight: 201.3<br>Appearance: Whitish powder<br>Melting point: 297-298° C.<br>Vapor pressure: $4.6 \times 10^{-4}$ mPa (25° C)<br>Solubility: | |
| | Solvent used | g/l 20° C. |
| | Water | 0.16 (pH4) 0.03 (pH7) |
| | n-Hexane | <0.01 |
| | Xylene | 0.13 |
| | Methanol | 8.28 |
| | Solvent used | g/l 20° C. |
| | 1,2-dichloroethane | 0.81 |
| | Acetone | 2.43 |
| | Ethyl acetate | 1.49 |
| | n-Octanol | 3.91 |
| Safety | Acute oral toxicity ($LD_{50}$: mg/kg) | Mouse 3,600<br>Rat 3,100<br>Rabbit 3,800 |
| | Acute percutaneous toxicity | Rabbit <2,000 |
| | Irritability | |
| | Skin | Rabbit Non-irritating |
| | Mucous membrane | Rabbit Non-irritating |
| | Antigenicity | Guinea pig None |
| | Target Organism | Acute oral toxicity $LD_{50}$ (mg/kg) |
| | Quail | <2,250 |
| | Mallard duck | 5,620 |
| | Target Organism | TLm (96 hrs), mg/l |
| | Bluegill | 19 |
| | Rainbow trout | 0.5 |

In the case of using thiabendazole as a rot-control or mildew-control composition, it is suitable to contain thiabendazole at, for example, 0.1 to 20% by mass, and preferably 1.0 to 15% by mass, with respect to the total mass of the pesticidal composition of the present invention in consideration of solubility in a solvent, and particularly a mixed solvent of a glycol-based solvent and methyl pyrrolidone. If the amount contained is 20% by mass or less, there is no risk of precipitation of crystals at low temperatures or when diluting with water, and if the amount contained is 0.1% by mass or more, adequate mildew-control effects can be expected to be obtained.

Examples of other pesticidal components used in the present invention include triazole-based fungicides components such as azaconazole, tebuconazole, propiconazole, cyproconazole, difenoconazole or mixtures thereof, having superior rot-control effects, pyrethroid-based insecticide components such as cyphenothrin, cypermethrin, permethrin and bifenthrin or mixtures thereof having superior insect preventive effects, (thia)nicotinyl-based insecticide components such as imidacloprid, acetamiprid, thiamethoxam and clothianidin or mixtures thereof, and other insecticide components such as etofenprox, silafluofen, fipronil and chlorfenapyr or mixtures thereof. Cyproconazole has particularly superior rot-control effects, while thiamethoxam is used preferably due to its superior insect preventive and ant-control effects.

The compounds thiabendazole (790), azaconazole (40), tebuconazole (761), propiconazole (675), cyproconazole (207), difenoconazole (247), cyphenothrin (206), cypermethrin (201), permethrin (626), bifenthrin (76), imidacloprid (458), acetamiprid (4), thiamethoxam (792), clothianidin (165), etofenprox (319), silafluofen (728), fipronil (354) and chlorfenapyr (130) are described, for example, in The e-Pesticide Manual, version 3.0, 13th Edition, Ed. CDC Tomlin, British Crop Protection Council, 2003-2004.

In the case of using these other pesticidal components, these other pesticidal components are preferably present at a ratio of, for example, 0.01 to 1.25 parts by mass, preferably 0.05 to 1.0 part by mass, and more preferably 0.05 to 0.5 part by mass, with respect to 1 part by mass of thiabendazole in consideration of pesticidal effects, safety and environmental contamination. In the case of using a combination of thiabendazole and a triazole-based fungicide component in particular, they are preferably contained at a mass ratio of thiabendazole and triazole-based fungicide component of 1:1 to 4:1.

The solvent used in the present invention is preferably a mixed solvent of a glycol-based solvent and methyl pyrrolidone. Examples of glycol-based solvents include methyl diglycol, ethyl diglycol, propyl diglycol, butyl diglycol, methyl glycol, ethyl glycol, ethylene glycol, diethylene glycol, polyethylene glycol, propylene glycol, polypropylene glycol, ethylene glycol monomethyl ether and propylene glycol monomethyl ether. In addition, methyl pyrrolidone is also referred to as N-methyl pyrrolidone and N-methyl-2-pyrrolidone.

The solvent of the present invention is suitably contained at, for example, 40 to 85% by mass, preferably 45 to 80% by mass, and more preferably 45 to 70% by mass, with respect to the total mass of the pesticidal composition of the present invention. If the amount contained is 40% by mass or more, the active ingredient of the present invention can be adequately dissolved, and if the amount contained is 85% by mass or less, the active ingredient can be contained to a degree that has adequate pesticidal effects, thereby making this preferable. Methyl pyrrolidone is suitably contained at, for example, 1 to 10% by mass and preferably 3 to 8% by mass, with respect to the total mass of the pesticidal composition of the present invention. In addition, methyl pyrrolidone is suitably used such that the mass ratio between the glycol-based solvent and methyl pyrrolidone is, for example, 1:0.5 to 1:4, and preferably 1:1 to 1:2.

Examples of the surfactant used in the present invention include nonionic surfactant and anionic surfactant. The surfactant may be used alone or a plurality of surfactants may be mixed.

Examples of nonionic surfactants include polyoxyethylene alkyl ethers, polyoxyethylene castor oil, hardened castor oil, fatty acid monoglycide, polyoxyethylene alkyl phenyl ethers, polyoxyethylene glycerin fatty acid esters, polyoxyethylene sorbitan fatty acid esters and propylene glycol fatty acid esters. In addition, examples of anionic surfactants include alkylbenzene sulfonates, alkylnaphthalene sulfonates, polyoxyethylene alkyl phenyl ether sulfates and polyoxyethylene alkyl ether sulfates. The surfactant of the present invention is suitably contained at, for example, 3 to 30% by mass and preferably 3 to 20% by mass with respect to the total mass of the pesticidal component of the present invention. If the amount contained is within the range of 3 to 30% by mass, adequate emulsification effects are obtained preferably.

Active ingredient stabilizers (such as antioxidants), colorants, rust preventives and so forth can be added to the composition of the present invention.

The pesticidal composition of the present invention can be prepared, for example, as indicated below. First, active ingredient in the form of 2-(thiazol-4-ine)benzimidazole and a mixed solvent of glycol-based solvent and methyl pyrrolidone are placed in a container and stirred to dissolve. Next, a surfactant is added followed by the addition of an emulsification stabilizer like lactic acid after which other components are added as necessary followed by stirring. At this time, the emulsification stabilizer is preferably added so that the pH of the pesticidal composition of the present invention is, for example, 3.0 to 5.5, and preferably 3.0 to 5.0. The aforementioned preparation is preferably carried out, for example, at a temperature of 0 to 30° C., and preferably at room temperature. The resulting pesticidal composition of the present invention preferably exists in a liquid state, and more specifically, as an emulsion in which the active ingredient is emulsified in water. Although varying according to the amount and efficacy of the active ingredient, the pesticidal composition of the present invention may be used without diluting or used after diluting with water by, for example, 5- to 50-fold, and preferably 10- to 30-fold, by volume at the time of use.

The following provides a more detailed explanation of the effects of the present invention using Reference examples, Examples and Comparative examples. However, the scope of the present invention is not particularly limited to such Examples.

In order to study the solubility of thiabendazole, the preferred active ingredient of the present invention, along with other pesticidal components in the form of cyproconazol and thiamethoxam, the tests described in Reference Examples 1 through 16 were carried out. It should be noted that KMC-113 (Kureha Chemical Industry) was used as the diisopropyl naphthalene, PEGM20M (number of moles added: 20, Nippon Nyukazai) was used as the polyethylene glycol (and the same was used in the examples of the present invention), EHDG (Nippon Nyukazai) was used as the diethylene glycol mono-2-ethylhexyl ether, and Diana solvent S (Idemitsu Kosan) was used as the isoparaffin. The blending ratios shown in the tables are in percent by mass. Solubility tests were conducted at normal temperature and under cooling for each reference example.

The solubility test at room temperature was evaluated by mixing, dissolving and stirring each component described in each reference example followed by allowing to stand undisturbed for 2 hours at normal temperature and then observing the solution state. Evaluation standards consisted of "○" in the case of no crystal precipitation (single liquid phase), and "x" in the case of crystal precipitation. The solubility test under cooling was conducted in the same manner as the testing at normal temperature with the exception of allowing to stand undisturbed for 24 hours at −5° C. instead of allowing to stand undisturbed for 2 hours at room temperature. Evaluation standards consisted of "○" in the case of a clear liquid free of crystal precipitation (single liquid phase), "Δ" in the case of liquid turbidity or phase separation, and "x" in the case of crystal precipitation. The results are shown in Table 2 below.

TABLE 2

Solubilitity tests at room temperature

| | | No. of Reference Example | | | | | | | | | | | | | | | |
|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 |
| Active Ingredient | Thiabendazole | | | 14.6 | 3.3 | 4 | 3 | 3 | 3 | | | 11.8 | 4 | 3.9 | 9.3 | 4.4 | 3.1 |
| | Cyproconazole | | 3.7 | | | | | | | | | | | 1.9 | 4.7 | 2.2 | 1.6 |
| | Thiamethoxam | 5 | | | | | | | | 32 | 3 | | | 1.9 | 4.7 | 2.2 | 1.6 |
| Solvent | N-methyl-2-pyrrolidone | | | 85.4 | | 30 | | | | 68 | | 88.2 | 36 | 41.8 | 81.3 | 91.2 | 63.9 |
| | Diisopropyl naphthalene | | | | | | | | | | | | | | | | |
| | Polyethylene glycol | 95 | 96.5 | | 96.7 | 66 | | | | | 97 | | 60 | 50.5 | | | |
| | Diethylene glycol mono-2-ethylhexyl ether | | | | | | | | | | | | | | | | 29.8 |
| | Isoparaffin | | | | | | | 97 | | | | | | | | | 29.8 |
| | xylene | | | | | | | | 97 | | | | | | | | 29.8 |
| Total (% by mass) | | 100 | 100 | 100 | 100 | 100 | 100 | 100 | 100 | 100 | 100 | 100 | 100 | 100 | 100 | 100 | 100 |
| Test Parameter | Solubility test at normal temperature | x | x | x | x | x | x | x | x | ○ | ○ | ○ | ○ | ○ | ○ | ○ | ○ |
| | Solubility test under cooling | x | x | x | x | x | x | x | x | x | x | x | x | x | x | ○ | ○ |

According to these results, Reference Examples 9 to 16 can be said to have a high degree of practicality, while Reference Examples 15 and 16 have a particularly high degree of practicality.

In order to examine the surfactants, which are able to be preferably used in the present invention, various surfactants were mixed with active ingredient and solvent of the present invention followed by evaluation of each of the resulting mixtures. The nonionic surfactants, anionic surfactants and mixtures thereof shown in Table 3 were used as the surfactants a sample of each Reference example were placed in a 200 ml ground-in stopper graduated cylinder followed by the addition of standard hard water at 20° C. to make a volume of 100 ml. The graduated cylinder was then repeatedly turned on its side and then righted 30 times at the rate of once every 2

TABLE 3

Nonionic surfactants, anionic surfactants and mixtures thereof used as the surfactants

| Product Name | Type | Main Component | Supplier |
|---|---|---|---|
| Newcol 564 | Nonionic | Polyoxyethylene alkyl phenyl ether | Nippon Nyukazai Co., Ltd. |
| Sanimal ALN | Nonionic, anionic | Alkylbenzene sulfonate, Polyoxyethylene alkyl aryl ether Polyoxyethylene castor oil ether | Nippon Nyukazai Co., Ltd. |
| Newcol 290K | Anionic | Dialkyl succinate sulfonate | Nippon Nyukazai Co., Ltd. |
| Sanimal 235 | Nonionic, anionic | Alkylbenzene sulfonate Polyoxyethylene alkyl phenyl ether | Nippon Nyukazai Co., Ltd. |
| Sanimal 280FL | Nonionic, anionic | Alkylbenzene sulfonate | Nippon Nyukazai Co., Ltd. |
| Newcol 565 | Nonionic | Polyoxyethylene alkyl phenyl ether | Nippon Nyukazai Co., Ltd. |
| New CALUGEN AD85 | | Dioctyl sulfosuccinate | Takemoto oil & fat. |
| New CALUGEN 1066 | | Polyoxyethylene nonyl phenyl ether | Takemoto oil & fat. |
| Newcol 2609 | Nonionic | Polyoxyethylene alkyl aryl ether | Nippon Nyukazai Co., Ltd. |
| TSS-04912 | Nonionic | Alpha-olefin sulfonate | Nippon Nyukazai Co., Ltd. |
| TS-7616 | Nonionic, anionic | Alkylbenzene sulfonate Polyoxyethylene alkyl aryl ether Polyoxyethylene alkyl ether | Nippon Nyukazai Co., Ltd. |
| Sanimal SFT | Nonionic, anionic | Polyoxyethylene alkyl ether Alkylbenzene sulfonate Polyoxyethylene alkyl aryl ether | Nippon Nyukazai Co., Ltd. |

Emulsification stability and solubility tests at normal temperature and under cooling were conducted on each of the Reference examples. The solubility tests at room temperature and under cooling used the same method as described in the Table 2. The emulsification stability test was conducted in accordance with the "1990 Edition of the Insecticide Guidelines" edited by the Second Examination Section of the Pharmaceutical Affairs Bureau of the Ministry of Health, Labor and Welfare, and the "Emulsification and Emulsification Stability Testing Methods" described on page 3 of the Nippon Yakugyo Shimbun (1990 Edition). More specifically, 5 ml of a sample of each Reference example were placed in a 200 ml ground-in stopper graduated cylinder followed by the addition of standard hard water at 20° C. to make a volume of 100 ml. The graduated cylinder was then repeatedly turned on its side and then righted 30 times at the rate of once every 2 seconds and then allowed to stand for 2 hours followed by observing the emulsified state of the solution to evaluate. The evaluation standards consisted of "○" in the case of satisfactory emulsification, "Δ" in the case of satisfactory emulsification immediately after turning the graduated cylinder on its side and then righting 30 times and solid phase separation occurring after standing undisturbed for 2 hours, and "x" in the case of the crystal precipitation starting immediately after turning the graduated cylinder on its side and righting 30 times and phase separation occurring after standing undisturbed for 2 hours. The blending ratios shown in the table are in percent by mass. The results are shown in Table 4 below.

TABLE 4

Solubility tests at normal temperature and under cooling and emulsification stability test

| | | Reference Example |||||||||||||| 
|---|---|---|---|---|---|---|---|---|---|---|---|---|---|---|
| | | 17 | 18 | 19 | 20 | 21 | 22 | 23 | 24 | 25 | 26 | 27 | 28 | 29 | 30 |
| Active Ingredient | Thiabendazole | 4 | 4 | 4 | 4 | 4 | 4 | 4 | 4 | 4 | 4 | 4 | 4 | 4 | 4 |
| | Cyproconazole | 2 | 2 | 2 | 2 | 2 | 2 | 2 | 2 | 2 | 2 | 2 | 2 | 2 | 2 |
| | Thiamethoxam | 2 | 2 | 2 | 2 | 2 | 2 | 2 | 2 | 2 | 2 | 2 | 2 | 2 | 2 |
| Solvent | N-methyl-2-pyrrolidone | 35 | 35 | 70 | 60 | 60 | 60 | 60 | 60 | 60 | 60 | 60 | 60 | 60 | 60 |
| | Diisopropyl naphthalene | | | | | 22 | 22 | 22 | 22 | 22 | 22 | 22 | 22 | 22 | 22 |
| | Polyethylene glycol | 47 | | | | | | | | | | | | | |
| | Diethylene glycol mono-2-ethyl hexyl ether | | 47 | | 22 | | | | | | | | | | |
| Surfactant | Newcol 564 | 10 | | | | | | | | | | | | | |
| | Sanimal ALN | | 10 | 22 | | | | | | | | | | | |
| | Newcol 290K | | | | 10 | | | | | | | | | | |
| | Sanimal 235 | | | | | 10 | 8 | | | | | | | | |
| | Sanimal 280FL | | | | | | | 10 | | | | | | | |
| | Newcol 565 | | | | | | 2 | | | | | | | | |
| | New CALUGEN AD85 | | | | | | | | 10 | | | | | | |
| | New CALUGEN 1066 | | | | | | | | | 10 | 10 | | | | |
| | Newcol 2609 | | | | | | | | | | | 10 | | | |
| | TSS-04912 | | | | | | | | | | | | 10 | | |

TABLE 4-continued

Solubility tests at normal temperature and under cooling and emulsification stability test

| | | Reference Example | | | | | | | | | | | | | |
|---|---|---|---|---|---|---|---|---|---|---|---|---|---|---|
| | | 17 | 18 | 19 | 20 | 21 | 22 | 23 | 24 | 25 | 26 | 27 | 28 | 29 | 30 |
| | TS-7616 | | | | | | | | | | | | | 10 | |
| | Sanimal SFT | | | | | | | | | | | | | | 10 |
| Total (% by mass) | | 100 | 100 | 100 | 100 | 100 | 100 | 100 | 100 | 100 | 100 | 100 | 100 | 100 | 100 |
| Test Parameter | Solubility test at normal temperature | ○ | ○ | ○ | ○ | ○ | ○ | ○ | ○ | ○ | ○ | ○ | ○ | ○ | ○ |
| | Solubility test under cooling | Δ | Δ | Δ | ○ | ○ | ○ | Δ | x | x | x | x | x | x | x |
| | Emulsification stability test | x | x | Δ | Δ | x | x | x | Δ | Δ | Δ | x | x | Δ | Δ |

In order to evaluate the pesticidal compositions of the present invention, various types of emulsification stabilizers, active ingredients, solvent and surfactant of the present invention were mixed, and various evaluations were performed on the resulting mixtures. Lactic acid, citric acid, succinic acid and benzoic acid were used as emulsification stabilizers of the present invention. In addition, ascorbic acid, tartaric acid, malic acid, phosphoric acid and formic acid were used as comparative examples. Thiabendazole, cyproconazole and thiamethoxam were used as active ingredients of the present invention. In addition, a mixed solvent of methyl diglycol (glycol-based solvent) and N-methyl-2-pyrrolidone (methyl pyrrolidone) was used as the solvent.

Solubility tests at normal temperature and under cooling, an emulsification stability test and an elapsed time stability test (during heating and at normal temperature) were conducted on each of the Examples and Comparative examples. The solubility tests at normal temperature and under cooling along with the emulsification stability test were conducted in the same manner as the methods described in Table 2 and Table 4 respectively.

The elapsed time stability test (heating) was performed in order to observe stability over time under severe conditions. The test was conducted by mixing, dissolving and stirring each component described in each Example and Comparative example, diluting 20-fold by volume with water, allowing to stand at 70° C. for 5 hours and then evaluating by observing the emulsified state of the solution. The evaluation standards consisted of:

○: maintaining a favorable emulsion

Δ: a certain degree of breakdown of the emulsion and phase separation x: breakdown of the emulsion and crystal precipitation.

The elapsed time stability test (room temperature) was performed in order to observe stability over time at room temperatures. The test was conducted by mixing, dissolving and stirring each component described in each Example and Comparative example, diluting 20-fold by volume with water, allowing to stand for 6 months at 45° C. and 75% RH and then evaluating by observing the emulsified state of the solution. Evaluations were made using as the standard the concentrations of all the pesticidal components of thiabendazole, thiamethoxam and cyproconazole being limited to within 90 to 110% by mass of their initial values. More specifically, the evaluation standards consisted of:

○: satisfying the standard after six months

Δ: satisfying the standard after 3 months but not after 6 months or the emulsion breaking down after 6 months x: not satisfying the standard even after 3 months The results are shown in Table 5 below. It should be noted that the blending ratios in the table are in percent by mass.

TABLE 5

Elapsed time stability test

| | | Examples and Comparative Examples (Comparative Examples are indicated with asterisks (*)) | | | | | | | | |
|---|---|---|---|---|---|---|---|---|---|---|
| | | 1 | 2 | 3 | 4 | 1* | 2* | 3* | 4* | 5* |
| Active Ingredient | Thiabendazole | 4 | 4 | 4 | 4 | 4 | 4 | 4 | 4 | 4 |
| | Cyproconazole | 2 | 2 | 2 | 2 | 2 | 2 | 2 | 2 | 2 |
| | Thiamethoxam | 2 | 2 | 2 | 2 | 2 | 2 | 2 | 2 | 2 |
| Emulsification Stabilizer | Lactic acid | 5 | | | | | | | | |
| | Citric acid | | 5 | | | | | | | |
| | Succinic acid | | | 5 | | | | | | |
| | Benzoic acid | | | | 5 | | | | | |
| | Ascorbic acid | | | | | 5 | | | | |
| | Tartaric acid | | | | | | 5 | | | |
| | Malic acid | | | | | | | 5 | | |
| | Phosphoric acid | | | | | | | | 5 | |
| | Formic acid | | | | | | | | | 5 |
| Solvent | Methyl diglycol | 47 | 47 | 47 | 47 | 47 | 47 | 47 | 47 | 47 |
| | N-methyl-2-pyrrolidone | 30 | 30 | 30 | 30 | 30 | 30 | 30 | 30 | 30 |
| Surfactant | Sanimal ALN | 10 | 10 | 10 | 10 | 10 | 10 | 10 | 10 | 10 |
| Total (% by mass) | | 100 | 100 | 100 | 100 | 100 | 100 | 100 | 100 | 100 |

TABLE 5-continued

Elapsed time stability test

| | | Examples and Comparative Examples (Comparative Examples are indicated with asterisks (*)) | | | | | | | |
|---|---|---|---|---|---|---|---|---|---|
| | | 1 | 2 | 3 | 4 | 1* | 2* | 3* | 4* | 5* |
| Test Parameter | Solubility test at normal temperature | ○ | ○ | ○ | ○ | ○ | x | x | x | x |
| | Solubility test under cooling | ○ | ○ | ○ | ○ | x | x | x | x | x |
| | Emulsification stability test | ○ | ○ | ○ | ○ | x | x | x | x | x |
| | Elapsed time stability test (heating) | Δ | Δ | ○ | ○ | ○ | Δ | x | Δ | x |
| | Elapsed time stability test (normal temperature) | ○ | ○ | Δ | Δ | x | x | x | x | x |

EFFICACY TEST EXAMPLE 1

A test was conducted in accordance with the Mildew-Control Efficacy Test of Wood Mildew-Control Agents of the Japan Wood Preserving Association Standards No. 2 (1995 Revision). More specifically, test pieces were prepared by treating pieces of beech wood with a test microorganism and treated specimen in accordance with the method described in the Japan Wood Preserving Association Standards No. 2 (1995 Revision) on pages 7-13 of the "Collection of Standards of the Japan Wood Preserving Association" (2001 Edition). The test pieces were then incubated, the growth status of the microorganisms was evaluated and the degree of damage (mold growth) was quantified. Mold growth was assessed using evaluation values consisting of a score of 0 for complete absence of mold growth on the test piece, a score of 1 for mold growth only on the sides of the test piece, a score of 2 for mold growth covering ⅓ or less of the surface area on the top of the test piece, and a score of 3 for mold growth covering more than ⅓ of the surface area on the top of the test piece. The average evaluation scores were calculated for each test microorganism followed by calculating the total average score ($S_1$). In addition, the total average score ($S_0$) was also determined for untreated specimens $F_1$ to $F_5$, and the degree of damage (D) (%) was determined using the following formula:

Degree of damage$(D)=(S_1)/(S_0) \times 100$

The test microorganisms used in this test consisted of *Aspergillus niger* (F1), *Penicillium funiculosum* (F2), *Aureabasidium pullulans* (F3), *Gliocladium virens* (F4) and *Rhizopus stolonifer* (F5).

The treated specimens used in the test consisted of the wettable powder, aqueous suspension and emulsion shown in Table 6 below diluted 10-fold or 20-fold by volume with distilled water. It should be noted that the emulsion corresponds to the pesticidal composition of the present invention. For the untreated specimens, the emulsion containing no thiabendazole in Table 6 was used.

TABLE 6

Treated specimens used in the Efficacy Test Example 1

| Name of component | Wettable powder (% by mass) | | Aqueous suspension (% by mass) | | Emulsion (% by mass) | |
|---|---|---|---|---|---|---|
| | 10-fold dilution | 20-fold dilution | 10-fold dilution | 20-fold dilution | 10-fold dilution | 20-fold dilution |
| Lactic acid | 5 | 5 | 5 | 5 | 5 | 5 |
| Thiabendazole | 2 | 2 | 2 | 2 | 2 | 2 |
| N-methyl-2-pyrrolidone | — | — | — | — | 30 | 30 |
| Methyl diglycol | — | — | — | — | Remainder | Remainder |
| Surfactant (Sanimal ALN) | 10 | 10 | 10 | 10 | 10 | 10 |
| Zeeklite*[1] | Remainder | Remainder | — | — | — | — |
| Processed starch*[2] | 30 | 30 | — | — | — | — |
| Polyvinyl pyrrolidone | 5 | 5 | 5 | 5 | — | — |
| Purified water | — | — | Remainder | Remainder | — | — |
| Total (% by mass) | 100 | 100 | 100 | 100 | 100 | 100 |

*[1]Zeeklite (Zeeklite Co., Ltd.)
*[2]PC-1000 (Nosan Corporation)

The results of Efficacy Test Example 1 are shown in Table 7.

TABLE 7

Efficacy Test Example 1

| Specimen | | | Average evaluation score per test microorganism* | | | | | Total evaluation score (S) | Degree of damage (D) (%) |
|---|---|---|---|---|---|---|---|---|---|
| | | | $F_1$ | $F_2$ | $F_3$ | $F_4$ | $F_5$ | | |
| Treated specimen | Wettable powder (% by mass) | 10-fold dilution | 2.2 | 2.0 | 1.8 | 2.0 | 2.3 | 10.3 | 72.5 |
| | | 20-fold dilution | 1.6 | 1.8 | 2.3 | 1.8 | 2.3 | 9.8 | 69.0 |
| | Aqueous suspension (% by mass) | 10-fold dilution | 2.0 | 2.3 | 2.1 | 2.3 | 2.0 | 10.7 | 75.4 |
| | | 20-fold dilution | 1.8 | 2.0 | 1.6 | 2.0 | 1.8 | 9.2 | 64.8 |
| | Emulsion (% by mass) | 10-fold dilution | 1.8 | 1.8 | 1.8 | 2.0 | 2.2 | 9.6 | 67.6 |
| | | 20-fold dilution | 1.5 | 1.5 | 1.6 | 1.8 | 1.8 | 8.2 | 57.7 |
| Untreated specimen (% by mass) | | | 3.0 | 2.5 | 2.7 | 3.0 | 3.0 | 14.2 | — |

*Test Microorganisms:
$F_1$: *Aspergillus niger*
$F_2$: *Penicillium funiculosum*
$F_3$: *Aureabasidium pullulans*
$F_4$: *Gliocladium virens*
$F_5$: *Rhizopus stolonifer*

According to these results, the emulsion of the present invention can be said to exhibit superior antimicrobial efficacy even when diluted 10- or 20-fold.

EFFICACY TEST EXAMPLE 2

A test was conducted in accordance with the Japan Wood Preserving Association Standards No. 2 (1995 Revision) in the same manner as Efficacy Test Example 1. The treated specimens used in the test consisted of the wettable powder and emulsion shown in Table 8 below diluted 20-fold by volume with water. It should be noted that the emulsion corresponds to the pesticidal composition of the present invention. For the untreated specimens, the emulsion containing no thiabendazole in Table 8 was used.

TABLE 8

Treated specimens used in the Efficacy Test Example 2

| Name of component | Wettable powder (% by mass) | Emulsion (% by mass) |
|---|---|---|
| Thiamethoxam | 2 | 2 |
| Cyproconazole | 2 | 2 |
| Thiabendazole | 4 | 4 |
| Surfactant (Sanimal ALN) | 4 | 10 |
| Lactic acid | — | 5 |
| N-methyl-2-pyrrolidone | — | 30 |
| Methyl diglycol | — | Remainder |
| Zeeklite*[1] | Remainder | — |
| Processed starch*[2] | 30 | — |
| Polyvinyl pyrrolidone | 5 | — |
| Total (% by mass) | 100 | 100 |

*[1]Zeeklite (manufacturer: Zeeklite Co., Ltd.)
*[2]PC-1000 (manufacturer: Nosan Corporation)

The specific evaluation method and calculation of degree of damage and other parameters are the same as in Efficacy Test Example 1. The results are shown in Table 9.

TABLE 9

Efficacy Test Example 2

| Specimen | | Average evaluation score per test microorganism* | | | | | Total evaluation score (S) | Degree of damage (D) (%) |
|---|---|---|---|---|---|---|---|---|
| | | $F_1$ | $F_2$ | $F_3$ | $F_4$ | $F_5$ | | |
| Treated specimens | Wettable powder (% by mass) | 0.5 | 0.8 | 1.0 | 0.8 | 0.7 | 3.8 | 22.4 |
| | Emulsion (% by mass) | 0.2 | 0.0 | 0.2 | 0.3 | 0.3 | 1.0 | 5.9 |
| Untreated specimen (% by mass) | | 3.7 | 3.2 | 2.8 | 3.8 | 3.5 | 17.0 | — |

*Test Microorganisms:
$F_1$: *Aspergillus niger*
$F_2$: *Penicillium funiculosum*
$F_3$: *Aureabasidium pullulans*
$F_4$: *Gliocladium virens*
$F_5$: *Rhizopus stolonifer*

According to these results, the emulsion of the present invention can be said to exhibit superior antimicrobial efficacy.

EFFICACY TEST EXAMPLE 3

A test was conducted in accordance with the Rot-Control Efficacy Test of Wood Rot-Control Agents for Coating, Spraying and Immersion Treatment of the Japan Wood Preserving Association Standards No. 1, No. 7 and No. 14 (1992). More specifically, test pieces were prepared by treating pieces of wood with samples prepared based on the indoor rot-control efficacy test and performance standards (JWPS-FW-S.1) of wood rot-control agents for surface treatment on pages 1-6 of the "Collection of Standards of the Japan Wood Preserving Association" (2001 Edition) published by the Japan Wood Preserving Association. Subsequently, in the case of the presence of a weather resistance procedure, the test pieces were subjected to (1) a volatilization procedure consisting of allowing to stand for 2 weeks in a constanttemperature chamber at 40° C.±2° C. and then (2) allowing to stand in a desiccator for about 30 minutes after drying for 48 hours at 60° C.±2° C. as described in "7.1 Weather-Resistance Procedure" of the same document, followed by measuring the mass ($W_3$). In the absence of a weather resistance procedure, the test pieces were (3) allowed to stand in a desiccator for about 30 minutes after drying for 48 hours at 60° C.±2° C. as described in "7.1 Weather-Resistance Procedure" of the same document, followed by measuring the mass ($W_3$). Moreover, the antimicrobial procedure described in "7.2 Antimicrobial Procedure" of the same document was carried out on the test pieces followed by measurement of mass ($W_4$), and the mass loss (%) was determined using the following formula:

Mass loss(%)=$(W_3-W_4)/W_3 \times 100$

It should be noted that the treated specimens and untreated specimens used in this test were the same as those used in the aforementioned Efficacy Test Example 2.

A composition was considered to demonstrate adequate rot-control performance if the mass loss was less than 3%. The results are shown in Table 10.

TABLE 10

Efficacy Test Example 3

| Specimen | Test microorganism | Wood | Weather resistance procedure | Mass loss (%) |
|---|---|---|---|---|
| Wettable powder | Tyromyces palustris | Cedar | Yes | 3.9 |
| | | | No | 2.7 |
| | Coriolus versicolor | Beech | Yes | 7.8 |
| | | | No | 5.4 |
| Emulsion | Tyromyces palustris | Cedar | Yes | 0.9 |
| | | | No | 0.0 |
| | Coriolus versicolor | Beech | Yes | 2.9 |
| | | | No | 1.1 |
| Untreated | Tyromyces palustris | Cedar | Yes | 29.5 |
| | | | No | 23.4 |
| | Coriolus versicolor | Beech | Yes | 37.7 |
| | | | No | 34.1 |

According to these results, the emulsion of the present invention is considered to demonstrate satisfactory rot-control performance.

The invention claimed is:

1. A stabilized pesticidal emulsifiable composition comprising a stabilizing effective amount of an emulsification stabilizer selected from the group consisting of lactic acid, glycolic acid, citric acid, succinic acid, benzoic acid and a mixture thereof, 2-(thiazol-4-ine) benzimidazole, a mixed solvent comprising a glycol-based solvent and methyl pyrrolidone, and a surfactant.

2. The pesticidal composition according to claim 1 further comprising a triazole fungicide component at a mass ratio of 1:1 to 4:1 between the 2-(thiazol-4-ine) benzimidazole and the triazole fungicide.

3. The pesticidal composition according to claim 1, wherein the glycol-based solvent is selected from methyl diglycol, ethyl diglycol, propyl diglycol, butyl diglycol, methyl glycol, ethyl glycol, ethylene glycol, diethylene glycol, polyethylene glycol, propylene glycol, polypropylene glycol, ethylene glycol monomethyl ether, propylene glycol monomethyl ether or mixtures thereof.

4. The pesticidal composition according to claim 2, wherein the triazole fungicide component is selected from azaconazole, tebuconazole, propiconazole, cyproconazole, difenoconazole or mixtures thereof.

5. The pesticidal composition according to claim 1, further comprising a pyrethroid insecticide component selected from cyphenothrin, cypermethrin, permethrin, bifenthrin, a (thia)nicotinyl insecticide component selected from imidacloprid, acetamiprid, thiamethoxam, clothianidin, an insecticide component selected from etofenprox, silafluofen, fipronil, chlorfenapyr or mixtures thereof.

6. A method for protecting industrial materials by controlling pests responsible for industrial materials damages, which comprises applying a pesticidal composition according to claim 1, to said industrial materials.

7. The pesticidal composition according to claim 1 wherein the emulsification stabilizer is present in an amount ranging from 2-8% by mass, with respect to the total mass of the composition.

8. The pesticidal composition according to claim 1 wherein the emulsification stabilizer is benzoic acid.

9. The pesticidal composition according to claim 1 wherein the emulsification stabilizer is lactic acid.

10. A method of stabilizing a pesticidal emulsion composition comprising 2-(thiazol-4-ine) benzimidazole, a mixed solvent comprising a glycol-based solvent and methyl pyrrolidone, and a surfactant, said method comprising the step of: adding an emulsification stabilizer selected from the group consisting of lactic acid, glycolic acid, citric acid, succinic acid, benzoic acid or a mixture thereof, in an amount ranging from 2-8% by mass, with respect to the total mass of the composition, whereby settling, precipitation and liquid phase separation of the 2-(thiazol-4-ine) benzimidazole emulsion after dilution with water is inhibited.

11. The method according to claim 9, wherein the composition comprises a 2-(thiazol-4-ine) benzimidazole and a triazole fungicide.

12. The method according to claim 9, wherein the emulsification stabilizer is benzoic acid.

13. The method according to claim 9, wherein the emulsification stabilizer is lactic acid.

14. A method for protecting industrial materials by controlling pests responsible for industrial materials damages, which comprises applying a pesticidal emulsion composition stabilized by the method according to claim 9 to said industrial materials.

* * * * *